United States Patent [19]
Cartledge

[11] Patent Number: 5,840,068
[45] Date of Patent: Nov. 24, 1998

[54] RAPID INFUSION SYSTEM

[76] Inventor: Richard G. Cartledge, 1800 Wesleyan Dr., 16, Macon, Ga. 31210

[21] Appl. No.: 608,291

[22] Filed: Feb. 28, 1996

[51] Int. Cl.[6] .................................................. A61M 37/00
[52] U.S. Cl. ........................................... 604/131; 604/151
[58] Field of Search .................................... 604/131, 151, 604/153

[56] References Cited

U.S. PATENT DOCUMENTS

| | | | |
|---|---|---|---|
| 4,012,177 | 3/1977 | Yakich | 604/153 X |
| 4,685,902 | 8/1987 | Edwards et al. | 604/151 X |
| 4,856,972 | 8/1989 | Van Benschoten et al. | 604/153 X |
| 4,950,136 | 8/1990 | Haas et al. | 604/153 X |

*Primary Examiner*—Wynn Wood Coggins
*Assistant Examiner*—Jennifer R. Sadula
*Attorney, Agent, or Firm*—Herbert M. Hanegan; Charles L. Warner, II; J. Rodgers Lunsford, III

[57] ABSTRACT

A rapid infusion system for rapidly delivering blood and/or volume expanding fluid to a patient, said rapid infusion device comprising in combination: a permanent portion and a removable portion; wherein said permanent portion includes an adjustable drive means and related control means therefor, wherein said removable portion includes sub-components that come into contact with the fluid infused to the patient, and optionally wherein said system can be portable.

15 Claims, 2 Drawing Sheets

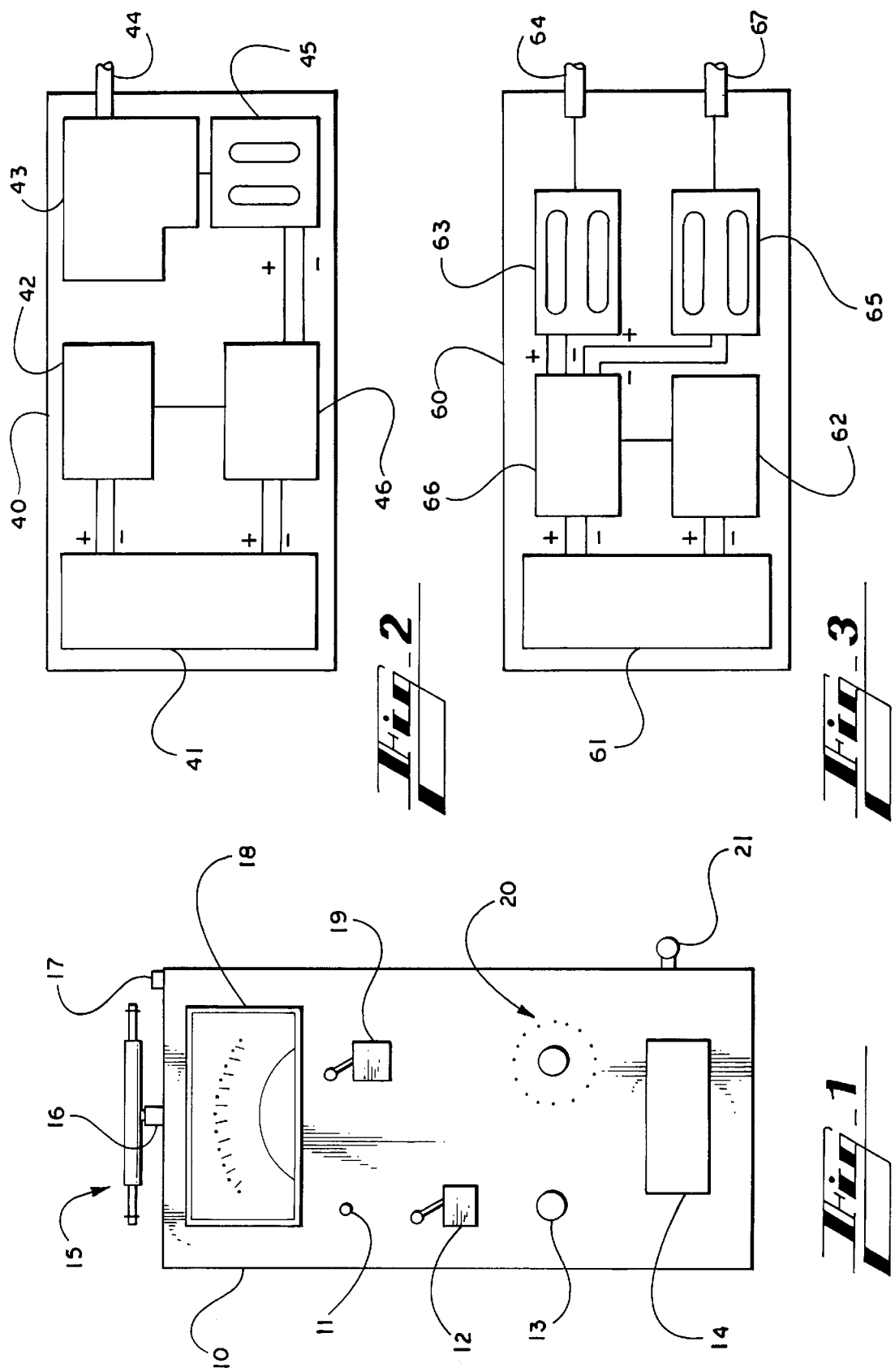

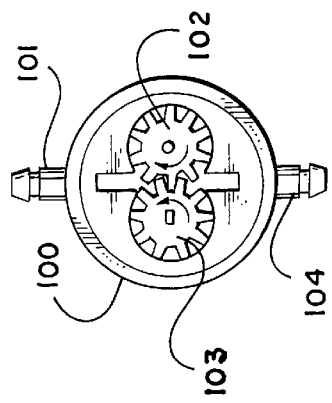
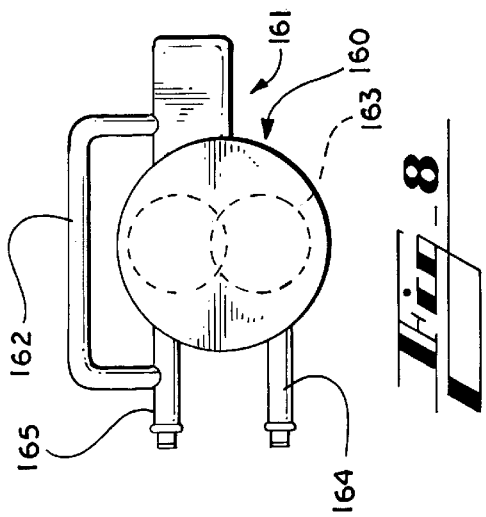
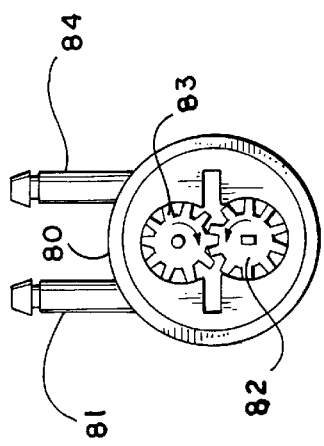
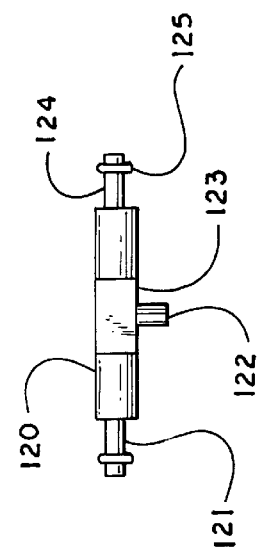
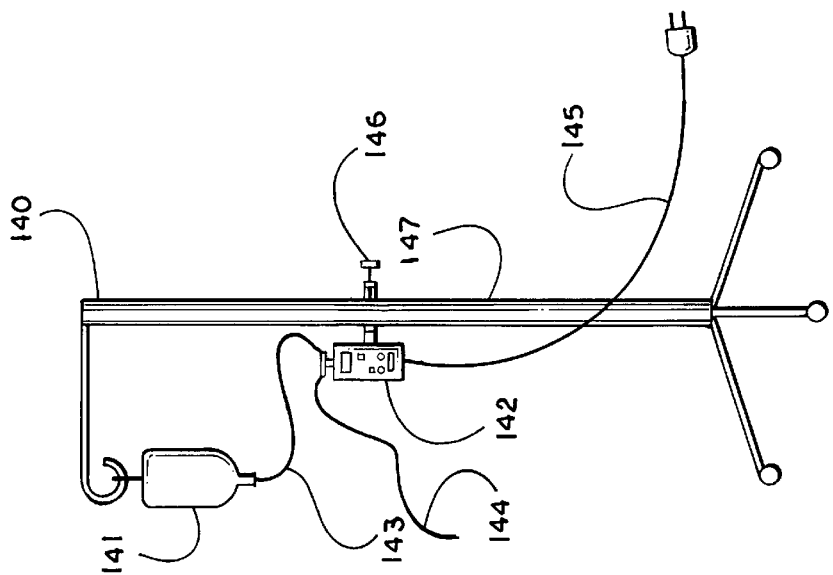

RAPID INFUSION SYSTEM

FIELD OF THE INVENTION

This invention relates to an apparatus for the rapid infusion of circulatory supportive fluids such as blood into a patient. The system comprises permanent components. The various components which physically come into contact with the fluid being infused can easily be removed and sterilized. The principal advantage achieved from this arrangement resides in the fact that it is small, lightweight, and portable. The system can be of a size to fit in a person's hand and is ideal for use by emergency personnel.

BACKGROUND OF THE INVENTION

During surgery or in the emergency room, it is frequently necessary to infuse blood or volume expanding fluids rapidly into a patient, particularly when massive blood losses have occurred. Patients having inadequate blood volume can suffer serious consequences.

There are many situations where large amounts of blood can be lost in a very short period of time, for example, in cases of serious automobile accidents, gun shot wounds in critical areas of the body, and a variety of major surgery including cancer surgery and heart and liver transplants.

In the past, the replacement of large amounts of blood loss has been a major problem to the surgical teams attending a suffering patient. A common method of rapid infusion includes the use of a plurality of infusion sites simultaneously. Infusion bags or bags of stored banked blood are interconnected by intravenous tubing. Frequently, a plurality of medical personnel are required to oversee the various infusion sites and to personally ensure the flow of blood from the blood bags.

Anesthesiologists are now regularly involved with cardiopulmonary resuscitation, trauma and organ transplantation procedures, and with maintenance of patient bodily functions during trauma and organ transplantation operations. During trauma and organ transplantation operations, patient blood loss cannot, practically speaking, be contained by the operating surgeon and must be replaced by the anesthesiologists standing in attendance. It is not uncommon for four to five anesthesiologists or technicians to stand in attendance during transplant operations lasting more than twenty-four hours attempting to infuse massive quantities of blood through five or six venous catheters.

Clinical records obtained from actual operations involving trauma and liver transplantations reveal blood losses estimated to be in excess of two hundred and fifty liters, a volume approximately fifty times a normal adult's total blood volume. Although it is not uncommon for an anesthesiologist or trauma surgeon to encounter massive exsanguination (ten liters and more) in a major trauma and transplantation center, it is, however, unusual to successfully resuscitate a patient with such massive blood volume loss with traditional methods.

Stephens, Jr., et al., U.S. Pat. No. 5,061,241, disclose a rapid infusion device capable of high volume pumping composed of two units. A permanent unit comprising a base portion which houses an AC/DC motor, a roller pump, and other associated gauges and switches. A disposable unit includes a filter reservoir, heat exchange component, and associated tubing leading to the roller pump. The roller pump increases the volume of fluid being pumped by increasing the rpm of the pumping unit and includes a pressure control valve.

Sassano, U.S. Pat. No. 4,747,826, discloses a portable infusion apparatus consisting of supply sources, reservoirs, and associated tubes and valves leading to an infusion pump which can either be a roller head occlusive or centrifugal pump.

SUMMARY OF THE INVENTION

With knowledge of the shortcomings of present day blood infusion apparatuses noted above, applicant has developed the rapid infusion system disclosed and claimed in the instant application.

An object of the present invention is the provision of an apparatus which would satisfy the various requirements of rapid infusion while at the same time reducing the number of medical and/or technical personnel required to monitor the equipment, a much desired improvement over presently known systems and practices used in critical life threatening situations.

A further object of the present invention to provide an adjustable system which is capable of high volume infusion of blood and/or volume expanding fluids into a patient.

BRIEF DESCRIPTION OF THE DRAWINGS

Referring to the drawings:

FIG. 1 is a front elevational view of the rapid infusion system.

FIG. 2 is a sectional view of one embodiment of the present invention with a covering or container wall removed.

FIG. 3 is a sectional view of another embodiment of the present invention with a covering or container wall removed.

FIG. 4 is a sectional view of a pump mechanism used in one embodiment of the present invention.

FIG. 5 is a sectional view of a pump mechanism used in another embodiment of the present invention.

FIG. 6 is a side view of a pump mechanism which connects to the rapid infusion unit.

FIG. 7 is a frontal view showing an I.V. pole, fluid bag and the rapid infusion system of the present invention.

FIG. 8 is a sectional view of the present invention showing the optional C.V.P. monitoring apparatus.

DESCRIPTION OF THE PREFERRED EMBODIMENTS

The rapid infusion of IV fluids has proven to save lives in patients suffering from blood loss. All rapid infusion devices presently available are large, heavy, prohibitively expensive, and extremely costly to operate because of special, extremely expensive, equipment that has to be discarded after each use. All of these devices include fluid warmers, adding to the unit's weight and size, and all operate using the same large, heavy, non-portable, roller pump mechanism. The prior art rapid-infusion devices cannot be used with typical peripheral IV cannulas but require large-bore central-line or venous cut-down catheters which can be inserted only by physicians. Although rapid infusion, or hyperinfusion, is a proven life saver, this technology is not commonly available to the public in most hospitals because of the aforementioned reasons.

The rapid infusion device of the present invention solves many problems present in prior art devices. It is small and portable, and if desired can be constructed so as to fit in the palm of your hand. It is inexpensive and can be potentially available to patients even in small rural hospitals. It can be used with any IV tubing or other commonly available hospital equipment and can generate equivalent or greater flow rates than existing rapid infusion devices. The present inventive device can be used with central lines, venous cut-down catheters, or peripheral IV's that nurses and paramedics can insert, therefore, it has potential application for use in ambulances, in the field, in emergency rooms, military applications, battlefield situations and the like.

The present inventive device is cost effective and environmentally friendly since the actual pump mechanism can be removed and sterilized, therefore nothing need be discarded or repurchased. The device can be used for blood transfusions imparting motion by a pressure change, i.e., it can add fluid to tubing which already contains the same or different fluid and thereby impart increased motion to the fluid already in the tubing without such fluid coming into contact with any portion of the device, therefore any pump mechanism can be used. The present invention also has excellent potential for military applications. Current hyperinfusion devices have no place in the military/battlefield areas. Their cost, size, lack of efficiency and lack of qualified field personnel preclude use of prior art hyperinfusion devices in such a setting.

Therefore, the military has no access to hyperinfusion technology due to the size, cost and complexity of current devices. The present invention is small and portable. It can be sized to fit in a person's hand and can be powered by A.C. or D.C. current. If powered by D.C. current, standard batteries can be used, including rechargeable batteries. Preferable when the infuser of the present invention is used in the field or in military applications, it can be less than about 5 inches by about 2.75 inches by about 2 inches, however the size is dependent upon the components used.

In patients suffering blood loss, measuring the pressure in the large central veins, (central venous pressure or C.V.P.) is the best method for assessing the efficacy of volume replacement. If the C.V.P. is low, the patient does not have adequate intravascular volume and thus further fluid recussitation is necessary. A high C.V.P. is an indication of volume overload and can result in heart failure and pulmonary edema (or fluid) in the lungs. Presently to measure C.V.P., a large catheter is placed in the patient's neck and connected to a pressure transducer which converts pressure changes into an electrical signal displayed on an oscilloscope-type monitor. Intensive care units and operating rooms are usually the only hospital areas capable of measuring C.V.P. In the ER setting, fluid administration is gauged empirically using only the patient's blood pressure and pulse to assess the adequacy of volume replacement. Hyperinfusion devices are best used while simultaneously monitoring C.V.P. The volume and rate of flow into the patient can then be quickly and accurately adjusted to sustain an adequate C.V.P., but the complications of heart failure and pulmonary edema from fluid overload are not eliminated due to human adjustment error. The hyperinfuser of the present invention can optionally infuse fluids and measure C.V.P. simultaneously through a single central venous catheter. The small device not only hyperinfuses fluid and monitors C.V.P., but can adjust the flow rate automatically to achieve any C.V.P. the physician desires. The present invention not only insures the ideal infusion rate for any particular patient, but is an inexpensive alternative to large, expensive C.V.P. monitors and obviates the need to place a second venous catheter dedicated only to C.V.P. readings. The present invention can include a dial to set the desired C.V.P., a screen that displays the actual C.V.P., and a mechanism that stops the pump at pre-set time intervals in order to accurately measure the C.V.P. The operator need only select how many times per minute the pump should stop, read the C.V.P., and adjust the flow rate accordingly. A manual mode is provided to infuse at a simple fixed rate with a switch that will halt the pump and give the operator an instantaneous C.V.P. reading. A control means may be optionally used which maintains the C.V.P. within a preset range. The adjustable pump means responds to signals from the control means and increases or decreases the fluid pressure and/or flow rate in response thereto. Advantageously, the inventive device has an alarm indicating when the IV fluid bag approaches empty.

The rapid infusion system is composed of two major portions. One portion includes permanent equipment, i.e., equipment which need not be sterilized and can be used over and over again, such as the pump motor and its related controls and optional equipment such as a C.V.P. monitor and related controls, optionally a heating element and related controls and attachment means. The other portion includes the removable components of the system such as the pump and pump gears or rollers, blood or fluid reservoir, valves and tubing.

The disclosed rapid infusion system is an adjustable mechanical pumping system for rapidly delivering blood and/or volume expanding fluids to a patient suffering from acute hypovolemia. The principle of operation of the disclosed invention is one of mechanically overcoming resistance. "Blood" is used herein to describe or refer to blood and/or volume expanding fluids delivered by the system since not only blood, but any other desired fluid may be delivered by the system. "Reservoir" as used herein includes one or more standard IV bags or separate container(s) where more practical than an IV bag.

The subject invention pertains to a novel system for rapid, venous infusion of a physiologic fluid, such as blood, which can include in combination a reservoir for the physiologic fluid having an inlet port for receiving the physiologic fluid and an outlet port for dispensing the physiologic fluid, an infusion pump to propel the physiologic fluid through the system, optional means for controlling the temperature of the physiologic fluid, optional means for filtering occlusive materials from the physiologic fluid, optional means for sensing the pressure of the physiologic fluid, means for infusing the physiologic fluid into a venous system and means for conveying the physiologic fluid to and from each of the components of the system.

In a preferred embodiment, the adjustable rapid infusion system comprises a reservoir having a capacity that can exceed several liters for holding a supply of physiologic fluid, the inventive infusion pump selected from the group consisting of a gear pump, a turbine pump, a roller head occlusive pump, a nonocclusive centrifugal pump and the like; optional portions such as a pressure controlling means, a temperature controlling means; a filter to remove any occlusive material from the physiologic fluid; a sensor for detecting the presence of air bubbles in the physiologic fluid in conjunction with means for cutting off the flow in the conduit in response to a detected air bubble. The pump advantageously is infinitely adjustable and can provide fluid flow rates from less than about 10 cc/minute to more than about 2000 cc/minute.

Optionally, the system may further include a temperature sensor at the output of the temperature controlling means for measuring and adjusting the physiologic temperature to maintain the temperature within acceptable limits. The system may also have readout means, which display fluid temperature, line pressure, fluid flow rate, and total volume of fluid infused.

The inventive system has a variable speed pump motor so that the amount of volume being pumped in can be increased merely by increasing the rpm of the motor. The reservoir may contain plural stages of filters and be provided with a plurality of inlets whereby volume from multiple sources can be fed into the reservoir to satisfy any high demand requirements of a patient. As set forth above, the system comprises a permanent portion and a removable and sterilizable portion. The removable portion includes pump gears and other components with which the volume comes into direct contact. The removable aspect of the invention provides an extra measure of protection against contamination to a subsequent patient.

Referring now in detail to FIG. 1, the rapid infusion device 10 comprises an on/off switch 11, a C.V.P. feedback mode on/off switch 12, a variable flow rate control 13 for use when C.V.P. is not being monitored and a liquid crystal display C.V.P. readout 14. Pump mechanism 15 is driven by and removably connected to device 10 by attachment to shaft 16. Optionally, pump mechanism 15 may be recessed within device 10 so that it does not extend outside device 10. Device 10 also includes a C.V.P. input jack 17, a fluid flow meter 18, an A.C./D.C. selector switch 19, a C.V.P. setting 20 for use in the feedback mode and an external supply/charger port 21.

FIG. 2 is a sectional view of one embodiment of the present invention wherein device 40 has a battery pack 41 connected to a central venous pressure feedback regulator 42. A drive gear box 43 for driving a pump mechanism (not shown) connected to a shaft 44 is driven by motor 45. Means to vary the resistance 46 is connected to battery pack 41 and motor 45 and can vary the speed of motor 44 and thus the rotational speed input to gear box 43 and the pump mechanism.

FIG. 3 is a sectional view of another embodiment of the present invention wherein device 60 has a battery pack 61, a C.V.P. regulator 62, a motor 63 with shaft 64, and a motor 65 with shaft 67. A means to vary the resistance 66 is connected to battery pack 61, C.V.P. regulator 62, motor 65 and motor 63, and can vary the speed of motors 63, 65, thereby varying the rotational speed input to the single or multiple pump mechanism(s) (not shown) which attaches to the shafts 64, 67.

FIG. 4 is a sectional view of one type of pump usable in an embodiment of the present invention. Pump 80 is attached to shaft 16 of device 10 which drives pump means 82 and 83, thereby imparting motion to fluid received from a reservoir through opening 81 and exiting through opening 84. As can be seen, the fluid goes through channels around the circumference of gear pump means 82 and 83.

FIG. 5 is a sectional view of one type of pump usable in another embodiment of the present invention wherein mechanism 100 is attached to shaft 16 of device 10 which drives pump means 103 and 102, thereby imparting motion to a fluid from a reservoir received through opening 101 and exiting through opening 104. As can be seen the fluid goes between pump means 102 and 103.

FIG. 6 is a side view of a pump mechanism usable with the present invention whereby shaft 122 is connected to shaft 16 of unit 10, thereby driving gear 123 which imparts motion to fluid received from a reservoir through opening 121 and exiting through opening 124. Raised shoulders 125 provides secure attachment to tubing or the like.

FIG. 7 is a typical I.V. arrangement 140 for hanging an I.V. bag 141 containing fluid which flows through tubing 143 to the rapid infusion device of the present invention 142. Device 142 is attached to pole 147 by attachment means 146 and imparts motion to the fluid from bag 141 and directs it through tubing 144. Device 142 may be powered by an external power source through cord 145.

FIG. 8 is a sectional view showing an optional C.V.P. monitoring system for the present invention. Pumping mechanism 160 contains a pressure probe 161 connected by a conduit 162 to the outlet 165 of the pumping mechanism. Fluid enters the pumping mechanism from a reservoir through inlet 164 whereby motion is imparted to the fluid by the pumping mechanism gears 163. The fluid pressure as it exits the pump is directed through outlet 165 and tubing 162 which communicates with pressure probe 161.

Unlike standard or traditional methods of intravenous fluid administration, the inventive rapid infusion system can provide continuous total replacement of adult human blood volume through any sort of hemorrhage, for an indefinite period of time and can rapidly regulate fluid temperature with minimal increase in resistance to flow, easily and rapidly administer massive quantities of blood to a single patient during a single operation, administer physiologic fluid maintained at a predetermined temperature at flow rates in excess of 2000 cc per minute, and permit simultaneous display and control of fluid temperature, flow rate, line pressure, and total volume of physiologic fluid administered. The system also is portable and able to be quickly and easily used in an emergency situation or by emergency personnel in the field. The blood delivered by the system can include clotting factors and can infuse an infinite amount of blood over an indefinite period of time based on the pump mechanism employed, the tubing sizes, etc., employed.

If desired the present invention can consist of multiple pumps infusing blood or the like to a patient through multiple catheters, thereby providing such fluids in volumes to the patient which are far in excess of that possible by present infusers.

While the invention has been described in its preferred embodiment, it is to be understood that the words which have been used are words of description rather than limitation and that changes may be made within the purview of the appended claims without departing from the scope or spirit of the invention.

What is claimed is:

1. A method for rapid infusion of a physiologic fluid into the venous system of a patient, comprising the steps of:
   a. providing a reservoir of a physiologic, fluid to be infused into a patient; and
   b. propelling the physiologic fluid from the reservoir into the venous system of a patient by an adjustable flow/rate portable infusion mechanism having a pump drive means for driving a pump means, said pump means being separable from the drive means.

2. The method of claim 1 which can provide fluid flow rates from about 10 cc/minute to about 2000 cc/minute.

3. The method of claim 1 wherein the flow rate is variably adjustable.

4. A power infuser comprising:
   a fluid conduit means having a proximal end and a distal end, the proximal end of said fluid conduit means containing at least one fluid reservoir,
   a propelling means for propelling the infusium, said propelling means in fluid communication with the at least one fluid reservoir through a connection at the distal end of said fluid conduit means, said propelling means including an adjustment means for selecting the fluid flow rate of the propelling means, said propelling means further comprising a pump means for imparting motion to the infusium, said pump means having a drive means for driving the pump means wherein the drive means does not contact the infusium and is separable from the pump means.

5. The power infuser of claim 4 which can provide fluid flow rates from about 10 cc/minute to about 2000 cc/minute.

6. The power infuser of claim 4 wherein the flow rate is variably adjustable.

7. The power infusion of claim 4 including a Y-connector in the fluid conduit to the patient providing branched conduits to the patient, the branched conduits each including means to provide communication with a separate intravenous infusion system and means for access with a syringe.

8. The power infuser of claim 4 wherein the fluid reservoir is of sufficient capacity to transfuse the entire blood volume of an adult patient.

9. The power infuser of claim 4 being of a size and weight such that it can be easily held while in use by a person.

10. The power infuser of claim 4 wherein said pump means is energized by D.C. current.

11. The power infuser of claim 10 wherein said pump means is energized by a battery selected from the group consisting of standard and rechargeable batteries.

12. The power infuser of claim 4 wherein said pump means is energized by A.C. current.

13. The power infuser of claim 4 having more than one pump means and the capability to infuse fluids into a person at multiple points and to infuse multiple types of fluids into a person.

14. The power infuser of claim 4 including means to measure the central venous pressure during infusion using a single venous catheter.

15. The power infuser of claim 14 including pump control means responsive to said central venous pressure measurement.

* * * * *